United States Patent [19]
Gregorovich et al.

[11] Patent Number: 5,932,667
[45] Date of Patent: Aug. 3, 1999

[54] REACTIVE ADDUCTS OF VINYLDIOXO COMPOUNDS

[75] Inventors: Basil V. Gregorovich, Wilmington, Del.; Isidor Hazan, Clementon, N.J.; Hisanori Omura, Farmington Hills, Mich.

[73] Assignee: E. I. du Pont de Nemours and Company, Wilmington, Del.

[21] Appl. No.: 08/670,956

[22] Filed: Jun. 26, 1996

Related U.S. Application Data

[63] Continuation-in-part of application No. 08/435,919, May 5, 1995, which is a continuation of application No. 08/186,090, Jan. 25, 1994, abandoned.

[51] Int. Cl.$^6$ .......................... C08F 283/00; C08G 77/06; C07D 319/06; C07D 305/00
[52] U.S. Cl. ........................... 525/477; 526/279; 528/15; 528/18; 549/214; 549/374
[58] Field of Search ...................................... 549/374, 214; 525/477; 526/279; 528/15, 18

[56] References Cited

U.S. PATENT DOCUMENTS

| | | | |
|---|---|---|---|
| 3,010,918 | 11/1961 | Ikeda | 260/17 |
| 3,010,923 | 11/1961 | Ikeda | 260/23 |
| 3,014,924 | 12/1961 | Brachman | 260/338 |
| 3,197,484 | 7/1965 | Ikeda | 260/340.7 |
| 3,373,160 | 3/1968 | Ikeda | 549/374 |
| 4,908,228 | 3/1990 | Lo | 549/214 |
| 5,107,008 | 4/1992 | Revis et al. | 556/425 |
| 5,571,931 | 11/1996 | Gregorovich | 549/374 |

OTHER PUBLICATIONS

Chemical Abstract vol. 115, No. 72383, Kuehling et al, "Synthesis of poly(2–ethyl–2–hydroxymethyltrimethylene carbonate", (1991).

Musavirov et al, Chemical Abstract vol. 99, No. 175,868, "New courses of synthesis & structure of 2,2–dimethyl–2–sila–1,3–dioxacyclohexanes" (1983).

Idel et al, Chemical Abstract vol. 94, No. 122 613, "Use of organosilicon used for stabilizing . . . polycarbonates" (1979).

*Primary Examiner*—John Kight
*Assistant Examiner*—Raymond Covington
*Attorney, Agent, or Firm*—James A. Costello; Sudhir G. Deshmukh

[57] ABSTRACT

Adducts of vinyldioxo compounds comprising a crosslinkable silyl-functional terminal group are disclosed. Such adducts are useful for preparing curable coating compositions.

19 Claims, No Drawings

REACTIVE ADDUCTS OF VINYLDIOXO COMPOUNDS

CROSS-REFERENCE TO RELATED APPLICATIONS

This is a continuation-in-part of application Ser. No. 08/435,919 filed on May 5, 1995 now abanonded, which is a continuation of application Ser. No. 08/186,090 filed on Jan. 25, 1994, now abandoned.

BACKGROUND OF THE INVENTION

This invention relates to reactive adducts of certain vinyldioxo compounds and to curable coating compositions comprising such reactive adducts.

Vinyldioxo compounds also referred to herein as VDO compounds) are well known and certain members of the class have been disclosed as polyester curing agents in U.S. Pat. No. 3,291,860. All are cyclic acetals, extensively studied and patented by Ikeda (U.S. Pat. Nos. 3,010,918; 3,010,923; 3,197,484), by Brachman (U.S. Pat. No. 3,014,924), and by others and described in detail by Hochberg (JOCCA 48, 11, 1043–1068, 1965). The simplest compounds in this class are made by a reaction of acrolein with a compound having two hydroxyl groups, either on adjacent carbon atoms or on carbon atoms separated by an additional carbon atom. When more than two hydroxyl groups are present in a compound, different pairs of hydroxyl groups can react with the aldehyde to form a cyclic acetal. Typical compounds having at least two hydroxyl groups include, for example, ethylene glycol, glycerin, 1,2,6-hexanetriol, and trimethylolpropane. Depending on the number and type of hydroxyl groups, the resulting VDO can be either a substituted 1,3-dioxolane or a substituted 1,3- dioxane, but frequently it is a mixture of a dioxolane with a dioxane. The reaction of acrolein (1) with trimethylolpropane (2) is shown below in Equation 1. The formation of VDO compounds, like other acetal-forming reactions, is catalyzed by acids.

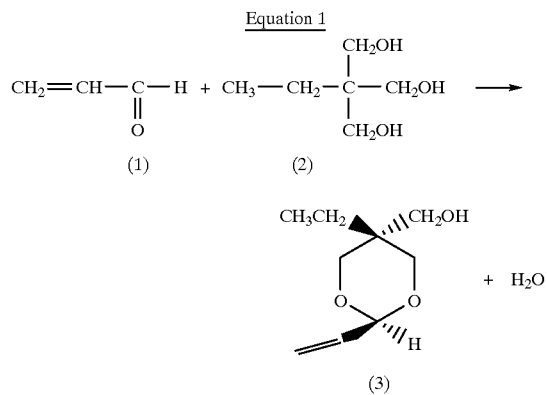

The reaction product according to formula (3) is a 2-vinyl-1,3-dioxane substituted with an ethyl group in the 4-position and with a hydroxymethyl (methylol) group in the 6-position. Analogous reactions can be used to prepare substituted rings having four to ten carbon ring members, that is, substituted dioxirane, dioxetane, dioxolane, dioxane, dioxepane, dioxocane, dioxonane, and dioxecane.

VDO compounds and their various derivatives have been described as useful polymerizable materials, which have the potential of providing both pigmented and clear-coat finishes in automotive and other applications. Those compounds polymerize in the presence of oxygen, such reactions being catalyzed by cobalt compounds. In an aqueous medium and in the presence of acids, the VDO compounds are unstable, so that further reactions are carried out in either a neutral, alkaline, or organic medium. Hochberg (op. cit.) discusses various syntheses and properties of many VDO compounds. In spite of the great industrial potential of VDO compounds, they have not been successfully commercialized in high performance coatings.

It has recently been found that VDO compounds can be polymerized, with ring opening, in the presence of an acid, as described in WO95/19975. For example, one of several reactions that may take place involves the above compound of formula (3) in the following equation 2:

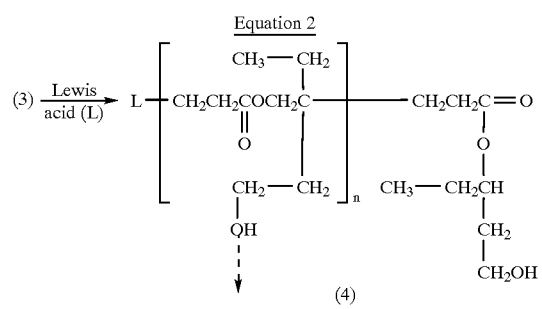

The hydroxyl group of the polymer attached to the repeating group in formula (4) can be used for crosslinking by reaction with a difunctional or polyfunctional compound to form a solid coating. This is done starting with a liquid component or with two liquid components, in the absence of a solvent or with a minimum amount of a solvent or diluent.

SUMMARY OF THE INVENTION

Acid rain damage and scratch and mar resistance of coatings have become major performance issues with coatings, particularly high gloss clearcoats such as those used on automobiles. It is known that crosslinking through alkoxysilane groups is useful in providing resistance to these damaging conditions. It has now been found that an adduct can be formed of a VDO compound with a compound (Z) having two reactive groups, at least one of which is an alkoxysilane or silicate under such conditions that only one group reacts, without crosslinking, or with a minimum amount of crosslinking; so that the adduct can be polymerized in the presence of catalyst, with ring opening, and undergo reaction or crosslinking through the second reactive group. For reaction to occur at least some of the groups must be hydrolyzable as shown below where X represents the adduct of VDO and a compound Z, and R is defined hereafter with respect to any of $R_2$ through $R_4$:

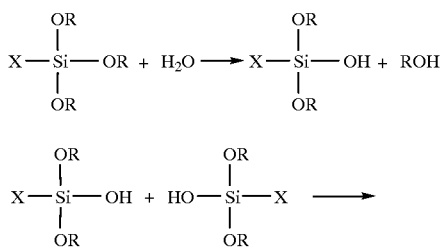

-continued

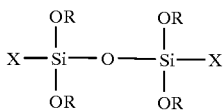

Although three alkoxy groups are shown on the silicon the number can be 1 to 3. In previous, simultaneous or subsequent reactions, the VDO ring portion of the X elements can open to produce polymers as shown previously. Subsequent reactions of other available alkoxy groups can occur to further enhance the crosslink network. These silicate crosslinks formed through the Z-group(s), are highly acid resistant. When more than one alkoxy site is available per silicon atom, the multi-branched networks produced by this type of crosslink site give coatings with excellent scratch and mar resistance.

According to the present invention, there is now provided a class of adducts of vinyldioxo compounds with difunctional compounds having two reactive functional groups, at least one of those functional groups being a silyl group, most preferably a di- or trialkoxysilyl group where the alkyl groups having from 1 to 4 carbon atoms, those adducts being represented by the following generic formula (5):

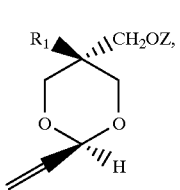

(5)

where $R_1$, is alkyl of 1 to 12 carbon atoms, preferably 1 to 6 carbon atoms, most preferably methyl or ethyl; or $R_1$ is branched or cyclic alkyl each of 3 to 12 carbons, preferably 5 or 6 carbons; Z is a divalent radical containing a terminal silyl group and is attached to the oxygen on the VDO. Also disclosed are new curable coating compositions comprising such adducts of vinyldioxo compounds.

DETAILED DESCRIPTION OF THE INVENTION

New adducts of VDO compounds are disclosed and have been found useful in silane coatings. These adducts can readily be formed using a starting VDO compound made from, for example, a vinyl aldehyde and a trihydroxyl compound. One such example is the vinyl-substituted dioxane made from acrolein and trimethylolpropane. When the VDO compound is made from acrolein and trimethylolpropane, as disclosed in WO95/19975, which is herein incorporated by reference in its entirety, then the $R_1$ substituent in the above formula (5) will be ethyl; when it is made from acrolein and trimethylolethane, $R_1$ will be methyl, etc.

The radical Z in the above formula (5) is derived from a compound consisting of a hydrocarbon moiety which can be aliphatic; branched aliphatic; cycloaliphatic; aromatic; a group capable of reacting with the hydroxyl group on the vinyldioxo molecule, such as isocyanate, chloro, acid, ester or anhydride; and a silyl group represented by $Si(R_2)(R_3)(R_4)$, wherein $R_2$, $R_3$, and $R_4$ are independently alkyl, phenyl, alkoxy or phenoxy. Preferably, two of the groups $R_2$, $R_3$, and $R_4$ on the silicon atom are hydrolyzable groups which can polymerize or crosslink by reaction with hydroxyl groups in polymers, oligomers or monomeric diols or polyols or by self-condensation in subsequent reactions under ambient or baking conditions. More preferably, at least two of $R_2$, $R_3$, $R_4$ are alkoxy, wherein each alkyl is as defined above with respect to $R_1$. A preferred silyl group is —Si$(R_5)(OR_6)OR_7)$, where $R_5$ is either $CH_3$, $CH_3CH_2$, $CH_3O$, or $CH_3CH_2O$; and $R_6$ and $R_7$ are independently $CH_3$ or $CH_3CH_2$.

Examples of the compounds which form the Z moiety when reacted with a VDO compounds are 3-isocyanatopropyl trimethoxysilane (according to formula 6 below) and silane oligomers (according to formula 7 below).

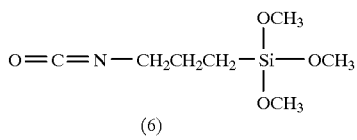

(6)

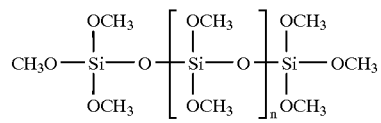

(7)

In formula 7 above, n can suitably be 0 to 50 or mixtures thereof, for example octamethoxytrisiloxane when n equals one. A commercially available mixture of such silane compounds is RDS-1™ (methylsilicate 51) supplied by Colcoat Co., Ltd. (Tokyo, Japan). This RDS-1 product is believed to be represented by formula 7 above when n is 1 to 3.

Based on formulas 6 and 7 above, for example, the corresponding adducts from a VDO compound (for example, obtained from trimethylolpropane and acrolein) can be represented by the following respective formulas 8 and 9.

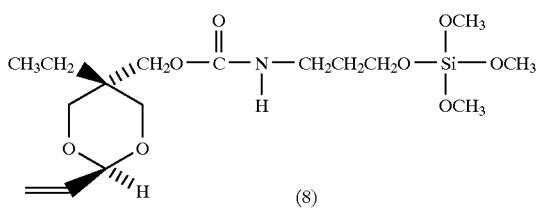

(8)

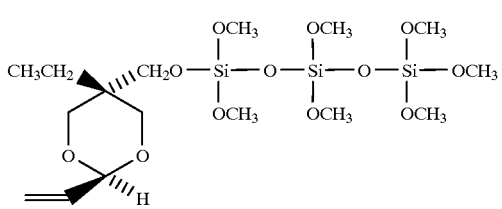

(9)

Similar compounds can be produced in which Z is the —CONH—$(CH_2)_n$—Si$(OCH_3)_3$ group in which n is 1 to 10, preferably 2 to 4 or in which Z is the —$[Si(OCH_3)_2]_n$—Si$(OCH_3)_3$ group wherein n is 0–10, preferably 1 to 4.

In the cases of adducts (8) and (9), each has a trimethoxysilyl end group, which can under proper conditions undergo further reactions. For example, in an acid-catalyzed polymerization of the VDO adduct, which is accompanied by ring opening, as shown above in Equation 2, some alkoxysilyl groups are hydrolyzed and new Si—O—Si bonds can form with another adduct or with a crosslinking agent or functional polymer in a coating composition. For example, silane and/or hydroxyl groups on a polymer may crosslink with the VDO adduct.

While the reaction of the starting VDO compound with a difunctional compound having end groups possessing different reactivities, such as compound (6), above, give essentially a single adduct compound quite readily, the reaction with compound (7) will result in a mixture of adduct products, which however, is also useful for coating applications and, in fact, may have the advantage of being less expensive to produce. Ideally, both types of reactions should be conducted under anhydrous conditions because water readily splits the methoxysilyl groups. Under those conditions, the isocyanate group of compound (6) reacts preferentially with the pendant methylol group of the starting VDO compound. Compound (7) will, of course, first react with one molecule of the VDO compound through one of its identical trimethoxysilyl groups. Theoretically, the remaining trimethoxysilyl group of either compound (6) or compound (7) could then further react with a second molecule of the VDO compound. Under anhydrous conditions and at low temperature and low catalyst, this second reaction can be largely avoided, although it usually occurs to a small extent.

The VDO adducts described above are useful as components of a curable coating composition for the purpose of lowering VOC (volatile organic compounds). Such compositions can comprise 10–80% by weight of a liquid organic carrier and 20 to 90% by weight, based on the weight of the compositions, of a binder. The VDO compounds are considered to be part of the binder (solids other than pigments in the composition). The binder can suitably comprise from 5 to 50% by weight of binder of the VDO adduct, 80 to 10% by, weight of binder of silane functional polymer, and an effective amount of a curing catalyst. The composition can suitably comprise a crosslinking agent, for example a melamine resin, a further VDO compound (without the Z moiety), a hydroxy functional polyol acrylic polymer, and/or a non-aqueous dispersed polymer or NAD. Other crosslinking agents are epoxy, isocyanate, and carbodiimide compounds or resins.

For these and other conventional components of a coating composition, further description is to be found in U.S. Pat. No. 5,244,696 hereby incorporated by reference in its entirety. As indicated therein, the silane-functional polymer may be an alkoxysilane functional acrylic polymer having a weight average molecular weight of 500 to 30,000 comprising from about 30 to 95% by weight, based on the weight of the polymer, of polymerized ethylenically unsaturated monomers which do not contain an alkoxysilane functionality and about 5 to 70% by weight of ethylenically unsaturated monomers which contain an alkoxysilane functionality. The silane-functional polymer may also have hydroxy-functional groups by copolymerizing monomers of hydroxy-functional esters of methacrylic or acrylic acid.

This invention is now illustrated by the following representative Examples. All parts and percentages are by weight unless otherwise indicated.

EXAMPLE 1

This example illustrates the preparation of a VDO adduct from 3-isocyanatopropyltrimethoxysilane. The 3-isocyanatopropyltrimethoxy silane (from OSI Specialties, Inc. of Tarrytown, N.Y.), 1498.62 g, 7.3 moles, was added slowly, with good mixing, under anhydrous conditions, to a flask containing 1498.38 g, 8.7 moles; of compound (3) and 3 g of DBTDL (dibutyl tin dilaurate). No solvent or diluent was used. The flask contents were heated over a period of 3 hours and 7 minutes form 21.5° C. to 101.7° C. Infrared spectra of the flask contents were taken at intervals to follow the progress of the reaction. The reaction was considered complete when the isocyanate peak was no longer detectable.

The reaction product was 100% solids material, useful as a reactive component of a silane resin-based coating system.

EXAMPLE 2

This example illustrates a coating composition comprising a VDO-6/isocyanate adduct according to the present invention. The isocyanate was 3-isocyanatopropyltrimethoxysilane. VDO-6 is another name for 2-vinyl-5-ethyl-5-hydroxymethyl-1,3-dioxane. The other components were analogous to corresponding components in U.S. Pat. No. 5,244,696, particularly in Examples 1 to 4, hereby incorporated by reference. A coating composition was prepared by blending together the following components:

| Component | Wt. % Solids | Parts by Weight |
| --- | --- | --- |
| Acrylosilane resin | 79.50 | 50.314 |
| NAD (non-aqueous dispersed resin) | 65.50 | 30.534 |
| VDO-6/isocyanate adduct | 100.00 | 18.10 |
| Cymel ™ 1161 melamine resin | 100.00 | 7.800 |
| Microgel rheology control agent | 70.00 | 7.429 |
| Silica rheology control dispersion | 34.20 | 8.772 |
| Resiflow ™ polybutyl acrylate flow agent | 50.00 | 0.400 |
| UV screeners (blend) | 32.50 | 4.00 |
| TMOA (trimethyl orthoacetate water scavenger) | 0.00 | 3.00 |
| DDBSA* | 44.99 | 2.778 |
| Tetrabutyl phosphonium chloride | 25.00 | 0.800 |
| Dibutyl tin dilaurate | 100.00 | 0.250 |

*Dodecyl benzene sulfonic acid, unblocked or blocked with AMP (aminomethylpropanol).

The final composition had a weight solids content of 68.97, a measured VOC of 2.85 lbs/gal and a calculated VOC of 2.62 lbs/gal, indicating very low loss of the VDO-6 adduct. The final viscosity was 95 cps (ICI Rheometer).

EXAMPLE 3

This example illustrates a coating composition comprising a VDO-6/RDS-1 adduct in a 1/1 weight ratio. RDS-1 is a methoxy silane compound commercially available for Colcoat Co., Inc. (Tokyo, Japan). VDO-6 is another name for 2-vinyl-5-ethyl-5-hydroxymethyl-1,3-dioxane. The other components were analogous to corresponding components in Example 2 above. A coating composition was prepared by blending together the following components:

| Component | Wt. % Solids | Parts by Weight |
|---|---|---|
| Acrylosilane resin | 79.50 | 45.031 |
| NAD (non-aqueous dispersed resin) | 65.50 | 30.534 |
| VDO-6/RDS-1 adduct | 100.00 | 18.100 |
| RDS-1 silane oligomer | 100.00 | 18.100 |
| Melamine resin | 100.00 | 7.800 |
| Microgel rheology control agent | 70.00 | 7.429 |
| Silica rheology control dispersion | 34.20 | 8.772 |
| Resiflow ™ polybutyl acrylate flow agent | 50.00 | 0.400 |
| UV screeners (blend) | 70.00 | 5.00 |
| DDBSA* | 44.99 | 2.778 |
| Tetrabutyl phosphonium chloride | 25.00 | 0.800 |
| Dibutyl tin dilaurate | 100.00 | 0.200 |

*Dodecyl benzene sulfonic acid, unblocked or blocked with AMP (aminomethylpropanol).

The final composition had a weight solids content of 76.17, a calculated VOC of 2.07 lbs/gal and final viscosity was 95 cps (ICI). The composition exhibited good application properties and appearance.

EXAMPLE 4

This example illustrates a coating composition comprising a VDO-6/RDs-1 adduct in a 2/1 weight ratio. RDS-1 is a methoxy silane compound commercially available from Colcoat Co., Inc. (Tokyo, Japan). VDO-6 is another name for 2-vinyl-5-ethyl-5-hydroxymethyl-1,3-dioxane. The other components were analogous to corresponding components in Example 2 above. A coating composition was prepared by blending together the following components:

| Component | Wt. % Solids | Parts by Weight |
|---|---|---|
| Acrylosilane resin | 79.50 | 50.314 |
| NAD (non-aqueous dispersed resin) | 65.50 | 30.534 |
| VDO-6/RDS-1 adduct | 100.00 | 18.100 |
| Melamine resin | 100.00 | 7.800 |
| Microgel rheology control agent | 70.00 | 7.429 |
| Silica rheology control dispersion | 34.20 | 8.772 |
| Resiflow ™ polybutyl acrylate flow agent | 50.00 | 0.400 |
| UV screeners (blend) | 32.50 | 12.308 |
| DDBSA* | 44.99 | 2.223 |
| Tetrabutyl phosphonium chloride | 25.00 | 0.800 |
| Dibutyl tin dilaurate | 100.00 | 0.250 |
| Methanol | 0.00 | 2.778 |

*Dodecyl benzene sulfonic acid, unblocked or blocked with AMP (aminomethylpropanol).

The final composition had a weight solids content of 68.97, a calculated VOC of 2.63 lbs/gal and final viscosity was 95 cps (ICI). This VDO-6 silicate 2/1 adduct is less volatile than the 1/1 adduct of the previous example.

The best mode presently contemplated for carrying out the invention is represented by the disclosure and claims herein, it being understood that selection of the best mode will depend on a variety of factors. Those skilled in the art will no doubt be able to compose numerous variations on the themes disclosed, such as changing the amounts of ingredients insignificantly from those shown, adding innocuous or supplementary substances, or substituting equivalent components for those shown. Such variations are considered to be within the inventive concept, as defined in the following claims.

We claim:

1. A compound which is an adduct of a vinyldioxo compound with a difunctional compound having two reactive functional groups, at least one of those functional groups being a silyl group, the adduct being represented by the following generic formula:

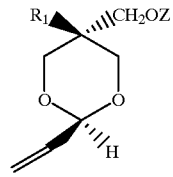

wherein $R_1$ is alkyl of 1 to 12 carbon atoms or branched or cyclic alkyl of 3 to 12 carbons atoms;

Z is a divalent radical comprising a terminal silyl group $Si(R_2)(R_3)(R_4)$, wherein $R_2$, $R_3$, and $R_4$ are independently selected from allyl, phenyl, alkoxy, and phenoxy, at least two of $R_2$, $R_3$, and $R_4$ being hydrolyzable groups that can react with hydroxyl groups and with themselves.

2. The compound of claim 1 wherein $R_1$ is methyl or ethyl.

3. The compound of claim 1 wherein two of $R_2$, $R_3$, and $R_4$ are alkoxy, wherein each alkyl is independently selected from the group alkyl of 1 to 12 carbon atoms, and branched and cyclic alkyl each having 3 to 12 carbon atoms.

4. The compound of claim 1 wherein Z is the —CONH—$(CH_2)_n$—$Si(OCH_3)_3$ group wherein n is 1 to 10.

5. The compond of claim 4 wherein n is 3.

6. The compound of claim 1 wherein Z is the —[Si$(OCH_3)_2]_n$—$Si(OCH_3)_3$ wherein n is 0 to 10.

7. The compound of claim 1 wherein the terminal silyl group has the formula $Si(R_5)(OR_6)(OR_7)$, wherein $R_5$ is selected from $CH_3$, $CH_3CH_2$, $CH_3O$ and $CH_3CH_2O$, and $R_6$ and $R_7$ are independently selected from $CH_3$ and $CH_3CH_2$.

8. A curable coating composition comprising 10 to 80% by weight of a liquid organic carrier and 20 to 90% by weight, based on the weight of the composition, of a binder wherein the binder comprises:

a) from 5 to 50% by weight of binder of an adduct of a vinyldioxo compound with a difunctional compound having two reactive functional groups, at least one of those functional groups being a silyl group, the adduct being represented by the following generic formula:

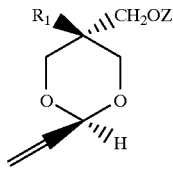

wherein R is alkyl having 1 to 12 carbon atoms or branched or cyclic alkyl having 3 to 12 carbon atoms, and Z is a divalent radical terminated by a silyl group; and b) 80 to 10% by weight of binder a silane functional polymer;

c) and an effective amount of a curing catalyst.

9. The composition of claim 8 wherein silyl group is $Si(R_2)(R_3)(R_4)$, wherein $R_2$, $R_3$, and $R_4$ are independently alkyl, phenyl, alkoxy, phenoxy, at least two of $R_2$, $R_3$, and $R_4$ being hydrolyzable groups.

10. The compositions of claim 8 wherein two of $R_2$, $R_3$, and $R_4$ are alkoxy, wherein each alkyl is independently selected form the group consisting of alkyl having 1 to 12 carbon atoms, branched alkyl of 3 to 12 carbon atoms and cyclic alkyl of 3 to 12 carbon atoms.

11. The composition of claim 8 wherein Z is the $-CONH-(CH_2)_n-Si(OCH_3)_3$ group wherein n is 1 to 10.

12. The composition of claim 8 wherein Z is the $-[Si(OCH_3)_2]_n-Si(OCH_3)_3$ group wherein n is 0 to 10.

13. The composition of claim 8, further comprising a crosslinking agent selected from the group consisting of epoxy, isocyanate, carbodiimide and melamine compounds or resins.

14. The composition of claim 13, wherein the crosslinking agent is melamine compound or resin.

15. The composition of claim 8, further comprising a VDO compound.

16. The composition of claim 8, further comprising a hydroxy functional polyol acrylic polymer.

17. The composition of claim 8 wherein the silane-functional polymer is an alkoxysilane functional acrylic polymer having a weight average molecular weight of 500 to 30,000 comprising about 30 to 95% by weight, based on the weight of the polymer, of polymerized ethylenically unsaturated monomers which do not contain an alkoxysilane functionality and about 5 to 70% by weight of ethylenically unsaturated monomers which contain an alkoxysilane functionality.

18. The composition of claim 12 wherein the silane-functional polymer has hydroxy-functional groups.

19. The composition of claim 8, further comprising a non-aqueous dispersed polymer.

* * * * *

UNITED STATES PATENT AND TRADEMARK OFFICE
CERTIFICATE OF CORRECTION

PATENT NO. : 5,932,667
DATED : August 3, 1999
INVENTOR(S) : Gregorovich et al.

It is certified that error appears in the above-identified patent and that said Letters Patent is hereby corrected as shown below:

Claim 1, Column 8, line 26, delete "allyl" and insert therefor -- alkyl --.

Signed and Sealed this

Twenty-second Day of May, 2001

Attest:

NICHOLAS P. GODICI

Attesting Officer     Acting Director of the United States Patent and Trademark Office